United States Patent
Lee et al.

(10) Patent No.: US 11,865,007 B2
(45) Date of Patent: Jan. 9, 2024

(54) CUSTOMIZED ARTIFICIAL TEMPOROMANDIBULAR JOINT UNIT

(71) Applicant: THE CATHOLIC UNIVERSITY OF KOREA INDUSTRY-ACADEMIC COOPERATION FOUNDATION, Seoul (KR)

(72) Inventors: Sang Hwa Lee, Seoul (KR); Joo Yup Lee, Seoul (KR)

(73) Assignee: THE CATHOLIC UNIVERSITY OF KOREA INDUSTRY-ACADEMIC COOPERATION FOUNDATION, Seoul (KR)

( * ) Notice: Subject to any disclaimer, the term of this patent is extended or adjusted under 35 U.S.C. 154(b) by 241 days.

(21) Appl. No.: 17/419,446

(22) PCT Filed: Dec. 20, 2019

(86) PCT No.: PCT/KR2019/018196
§ 371 (c)(1),
(2) Date: Jun. 29, 2021

(87) PCT Pub. No.: WO2020/141774
PCT Pub. Date: Jul. 9, 2020

(65) Prior Publication Data
US 2022/0142782 A1    May 12, 2022

(30) Foreign Application Priority Data
Dec. 31, 2018  (KR) ........................ 10-2018-0173545

(51) Int. Cl.
*A61F 2/30*  (2006.01)

(52) U.S. Cl.
CPC .. *A61F 2/3099* (2013.01); *A61F 2002/30242* (2013.01); *A61F 2002/30331* (2013.01);
(Continued)

(58) Field of Classification Search
CPC ..................... A61F 2/30; A61F 2/3009; A61F 2002/30991; A61F 2002/30993; A61F 2002/30383; A61F 2002/30331
See application file for complete search history.

(56) References Cited

U.S. PATENT DOCUMENTS 10,022,235 B2    7/2018  Vogt
10,117,747 B2 *  11/2018 Dubois ................. A61F 2/3099
2011/0224673 A1  9/2011  Smith

FOREIGN PATENT DOCUMENTS

KR    10-2005-0015625 A    2/2005
KR    10-2010-0100157 A    10/2010
(Continued)

OTHER PUBLICATIONS

International Search Report for PCT/KR2019/018196 dated Aug. 28, 2020.

*Primary Examiner* — Brian A Dukert
(74) *Attorney, Agent, or Firm* — The PL Law Group, PLLC (57) ABSTRACT

A customized artificial temporomandibular joint unit according to an embodiment of the present disclosure includes a first plate provided along a lower line of a lower jawbone forming a temporomandibular joint and having an insertion groove that is outwardly open, a second plate provided at a temporal bone forming the temporomandibular joint together with the lower jawbone, and a main prosthesis detachably combined to the first plate without a separate fastening device by being forcibly fit into the insertion groove while approaching the first plate, and arranged in a customized manner at a facing surface location facing the second plate.

4 Claims, 8 Drawing Sheets

(52) U.S. Cl.
CPC ............... *A61F 2002/30383* (2013.01); *A61F 2002/30604* (2013.01); *A61F 2002/30991* (2013.01); *A61F 2002/30993* (2013.01)

(56) References Cited

FOREIGN PATENT DOCUMENTS

| | | | |
|---|---|---|---|
| KR | 10-1370427 | B1 | 3/2014 |
| KR | 10-2017-0133591 | A | 12/2017 |
| WO | WO 2008/061769 | A2 | 5/2008 |

\* cited by examiner

CUSTOMIZED ARTIFICIAL TEMPOROMANDIBULAR JOINT UNIT

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2019/018196, filed Dec. 20, 2019, which claims priority to the benefit of Korean Patent Application No. 10-2018-0173545 filed in the Korean Intellectual Property Office on Dec. 31, 2018, the entire contents of which are incorporated herein by reference.

TECHNICAL FIELD

The present disclosure relates to a customized artificial temporomandibular joint unit, and more particularly, to a customized artificial temporomandibular joint unit having an improved structure such that it is easy to mold a product corresponding to a shape and angle of a temporomandibular joint different for each individual and it is possible to replace only a part required to be replaced due to abrasion or the like after a procedure.

BACKGROUND ART

Figure 1:
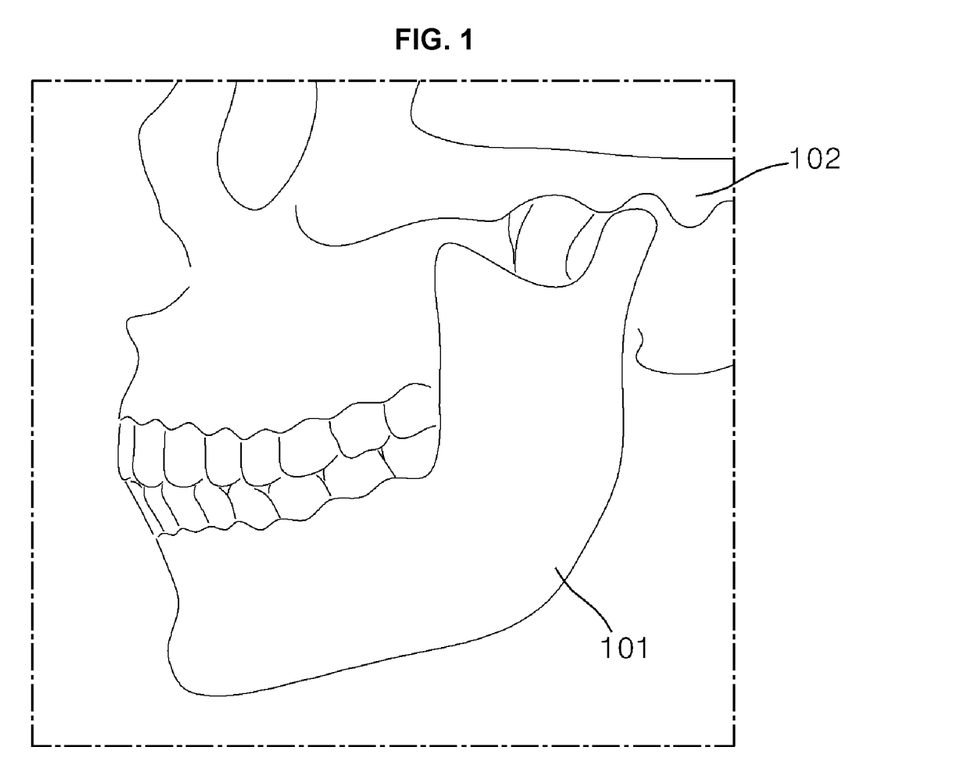
FIG. 1 is a view of a temporomandibular joint structure of a human body.

Temporomandibular joints are sole joints of a facial part, which can be determined to move when a mouth is opened while both fingers are placed in front of external acoustic meatuses (external auditory canals), as shown in FIG. 1. A skull of a person has a structure in which several bones are interlocked with each other to protect a brain, and thereamong, there are concavities called mandibular fossae (glenoid fossae, in contact with mandibles) below left and right temporal bones 102 covering the sides of a head.

The temporomandibular joints are allowed to move as both head parts of a lower jawbone 101 having a convex shape are fitted to the concavities. The temporomandibular joints are joints where the temporal bones 102 and the lower jawbone 101 are engaged. A discus articularis (disc) that is a fibrous tissue is present between two bones to function as a buffer for preventing the bones from directly contacting each other. Also, a joint capsule (articular capsule) surrounding a joint contains synovia acting as a lubricant therein, thereby reducing friction during movement of the joint and enabling smooth movement.

Figure 2:
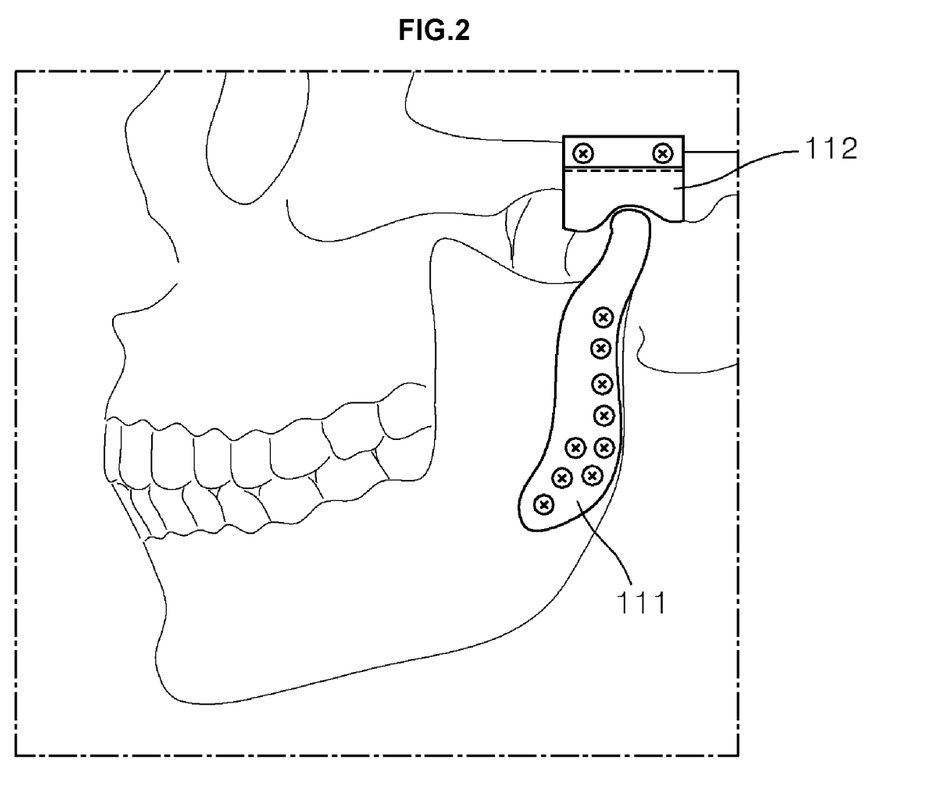
FIG. 2 is a view for describing a general artificial temporomandibular joint unit.

However, various joint diseases may be observed in the temporomandibular joint like other joints, and in some cases, artificial joint surgeries as shown in FIG. 2 have been frequently performed in addition to conservative cares and conservative operations.

Instruments used for the artificial joint surgery have following issues.

In other words, as shown in FIG. 2, an artificial joint unit according to the related art includes a first plate 111 provided at the lower jawbone 101 and a second plate 112 provided at the temporal bone 102.

Because such an artificial joint unit is generally a ready-made product having a standardized structure, products corresponding to different shapes and angles of temporomandibular joints of patients are unable to be applied to the patients, resulting in difficulties in procedures and inconvenience of the patients. Also, the entire first plate 111 or second plate 112 needs to be replaced when replacement is required due to abrasion or the like after the procedure.

SUMMARY

Provided is a customized artificial temporomandibular joint unit, wherein it is easy to mold a product corresponding to a shape and angle of a temporomandibular joint different for each individual and it is possible to replace only a part required to be replaced due to abrasion or the like after a procedure.

According to an embodiment of the disclosure, a customized artificial temporomandibular joint unit includes a first plate provided along a lower line of a lower jawbone forming a temporomandibular joint and having an insertion groove that is outwardly open, a second plate provided at a temporal bone forming the temporomandibular joint together with the lower jawbone, and a main prosthesis detachably combined to the first plate without a separate fastening device by being forcibly fit into the insertion groove while approaching the first plate, and arranged in a customized manner at a facing surface location facing the second plate.

The main prothesis may include a combining portion forcibly fit into the insertion groove of the first plate, and a convex portion extending from the combining portion towards the second plate and having a surface facing the second plate convex in a ball shape, wherein the combining portion of the main prothesis may have a tapered shape such that a width decreases towards the convex portion, and the insertion groove of the first plate may have a shape corresponding to the combining portion.

The first plate may include a jamming groove portion formed on a surface defining the insertion groove, and the main prothesis may include a jamming embossing inserted into the jamming groove portion.

The customized artificial temporomandibular joint unit may further include a sub-prothesis detachably combined to the second plate and having a facing surface to the main prothesis arranged to face the main prothesis.

The customized artificial temporomandibular joint unit may further include a fitting groove formed on the second plate, and a fitting protrusion protruding at the sub-prothesis to be detachably combined to the fitting groove.

A customized artificial temporomandibular joint unit, according to the disclosure, is configured such that a ready-made product, such as a first plate, is used as a main part forming rigidity of an artificial temporomandibular joint, a main prothesis is formed to be a part that is expected to be replaced due to abrasion and required to be customized according to a structure and angle of a temporomandibular joint slightly different for each person, and the main prothesis is used to be combined to or separated from the ready-made product. Accordingly, not only it is possible to manufacture a patent-customized artificial temporomandibular joint, but also it is possible to provide a high-quality medica service by replacing only a part that is required to be replaced due to abrasion or the like after a procedure.

DETAILED DESCRIPTION

In the following description, for clear understanding of the disclosure, a description about well-known technology regarding features of the disclosure will be omitted. Embodiments described below are to help understanding of the disclosure, and it is obvious that the embodiments do not limit the scope of the disclosure. Thus, an equivalent performing same functions as the disclosure will also belong to the scope of the disclosure.

In the following description, same reference numerals denote same components, and unnecessary redundant descriptions and descriptions about well-known technology will be omitted. In addition, descriptions about each embodiment of the disclosure, which overlap those about the background art, will also be omitted.

Hereinafter, a customized artificial temporomandibular joint unit according to an embodiment of the disclosure will be described in detail with reference to the accompanying drawings.

Figure 3:
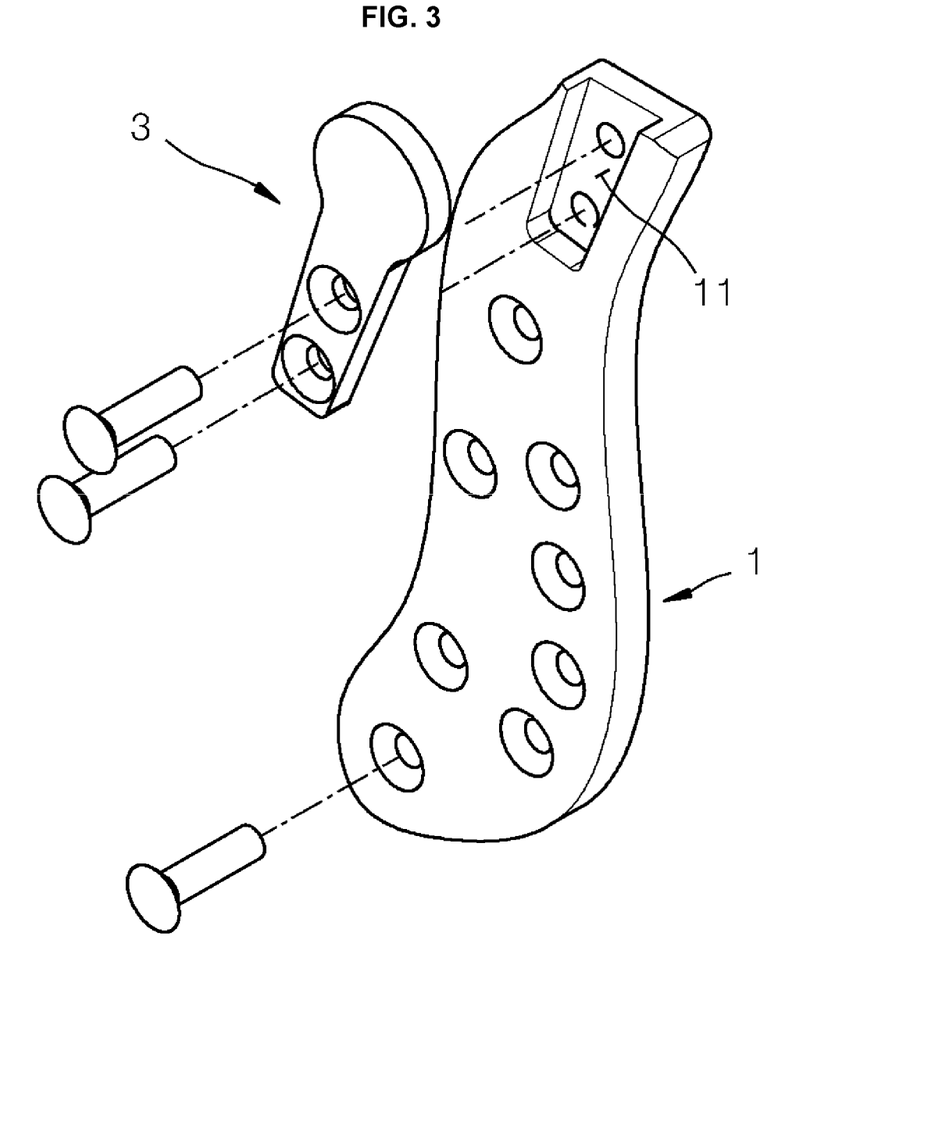
FIG. 3 is an exploded perspective view of a first plate and a main prothesis, according to an embodiment of the disclosure.
Figure 4:
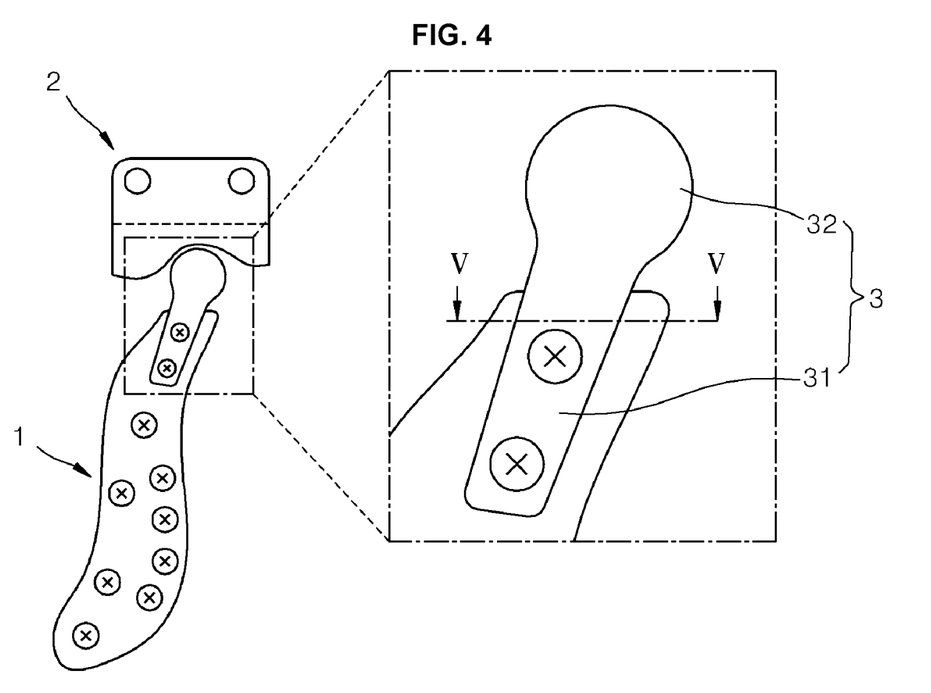
FIG. 4 is a side view of an installation state according to an embodiment of the disclosure.
Figure 5:
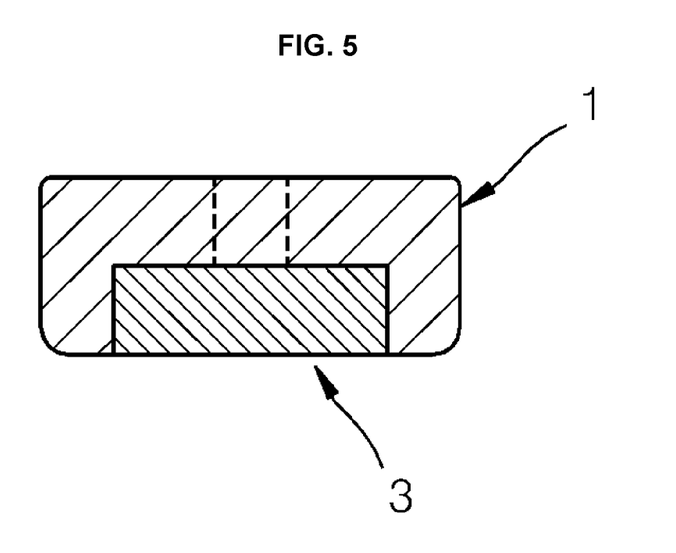
FIG. 5 is a cross-sectional view taken along a line V-V of FIG. 4.

FIG. 3 is an exploded perspective view of a first plate 1 and a main prothesis 3, according to an embodiment of the disclosure, FIG. 4 is a side view of an installation state according to an embodiment of the disclosure, and FIG. 5 is a cross-sectional view taken along a line V-V of FIG. 4.

A shown in FIGS. 3 and 4, the customized artificial temporomandibular joint unit according to an embodiment of the disclosure is provided at a lower jawbone and a temporal bone to assist an abrased or damaged temporomandibular joint, and includes the first plate 1, a second plate 2, and the main prothesis 3.

The first plate 1 is formed of a metal material, such as stainless steel or titanium, or a synthetic resin material, such as ceramic with satisfactory rigidity, and includes an insertion groove 11 that is outwardly open and provided along a lower line of a lower jawbone forming a temporomandibular joint by being formed in a shape corresponding to the lower line. Here, as shown in FIG. 5, the main prothesis 3 is inserted into and combined to the insertion groove 11.

The second plate 2 is provided at the temporal bone that forms the temporomandibular joint together with the lower jawbone, and may be formed of the same material as the first plate 1 or may be formed of a resin material with shock absorbability at a portion contacting the main prothesis 3 and a rigid material at a remaining portion.

The main prothesis 3 is for forming, together with the first plate 1, an artificial temporomandibular joint corresponding to a shape or angle of a joint different for each person, and may be detachably combined to the first plate 1 without a separate fastening device, by being forcibly fit into the insertion groove 11 while approaching the first plate 1, may secure additional fixability in addition to screw fixation, and is arranged at a location facing the second plate 2.

The main prothesis 3 may be formed of a metal material, such as stainless steel or titanium, or a synthetic resin material, such as ceramic with satisfactory rigidity, like the first plate 1, or in some cases, may be formed of a resin material with shock absorbability at an articular surface of a convex portion reproducing a condylar part, and various materials, such as a rigid material, at a remaining portion.

The main prothesis 3 may be customized, together with the insertion groove 11 of the first plate 1, according to a shape or angle of a temporomandibular joint different for each patient, and may be replaced and used without having to replace the first plate 1, even during abrasion caused by contact with the second plate 2 with the lapse of time after a procedure.

The customized artificial temporomandibular joint unit having such a structure, according to an embodiment of the disclosure, is configured such that a ready-made product, such as the first plate 1, or a customized part in some cases, is used as a main portion forming rigidity of an artificial temporomandibular joint, the main prothesis 3 is formed to be a part that is expected to be replaced due to abrasion and required to be customized according to a structure and angle of a temporomandibular joint slightly different for each person, and the main prothesis 3 is able to be used while being combined to or separated from the ready-made product, thereby enabling manufacture of a patient-customized artificial temporomandibular joint. In addition, the customized artificial temporomandibular joint unit is able to provide a high-quality medical service because only a part that is required to be replaced due to abrasion or the like after a procedure is replaced.

As shown in FIG. 4, the main prothesis 3 includes a combining portion 31 forcibly fit to the insertion groove 11 of the first plate 1, and a convex portion 32 extending from the combining portion 31 to the second plate 2 and having a surface facing the second plate 2 convex in a ball shape.

Figure 6:
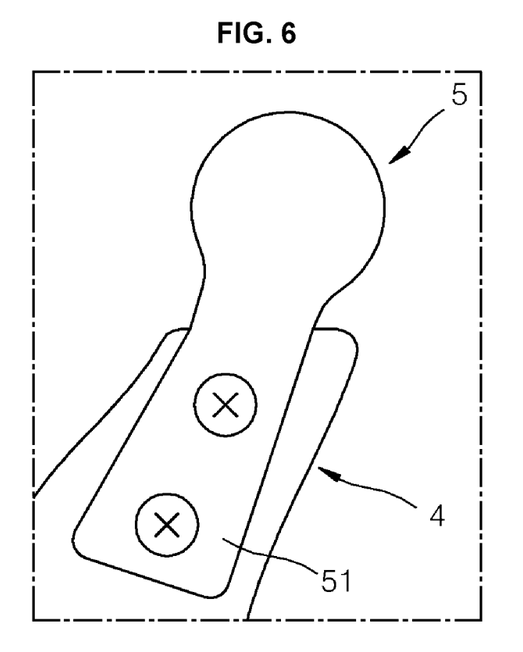
FIG. 6 is a side view of a first plate and a main prothesis, according to another embodiment of the disclosure.

FIG. 6 is a side view of a first plate 4 and a main prothesis 5, according to another embodiment of the disclosure.

In the present embodiment of FIG. 6, a combining portion 51 of the main prothesis 5 has a tapered shape in which a width decreases towards a convex portion of the main prothesis 5, and an insertion groove of the first plate 4 has a shape corresponding to the combining portion 51.

According to the present embodiment having such a structure, the combining portion 51 of the main prothesis 5 and the insertion groove of the first plate 4 are combined in a tapered shape even when a force is applied to the main prothesis 5 towards a second plate, and thus the combining portion 51 and the insertion groove strongly maintain a combined state without being detached from each other.

Figure 7:
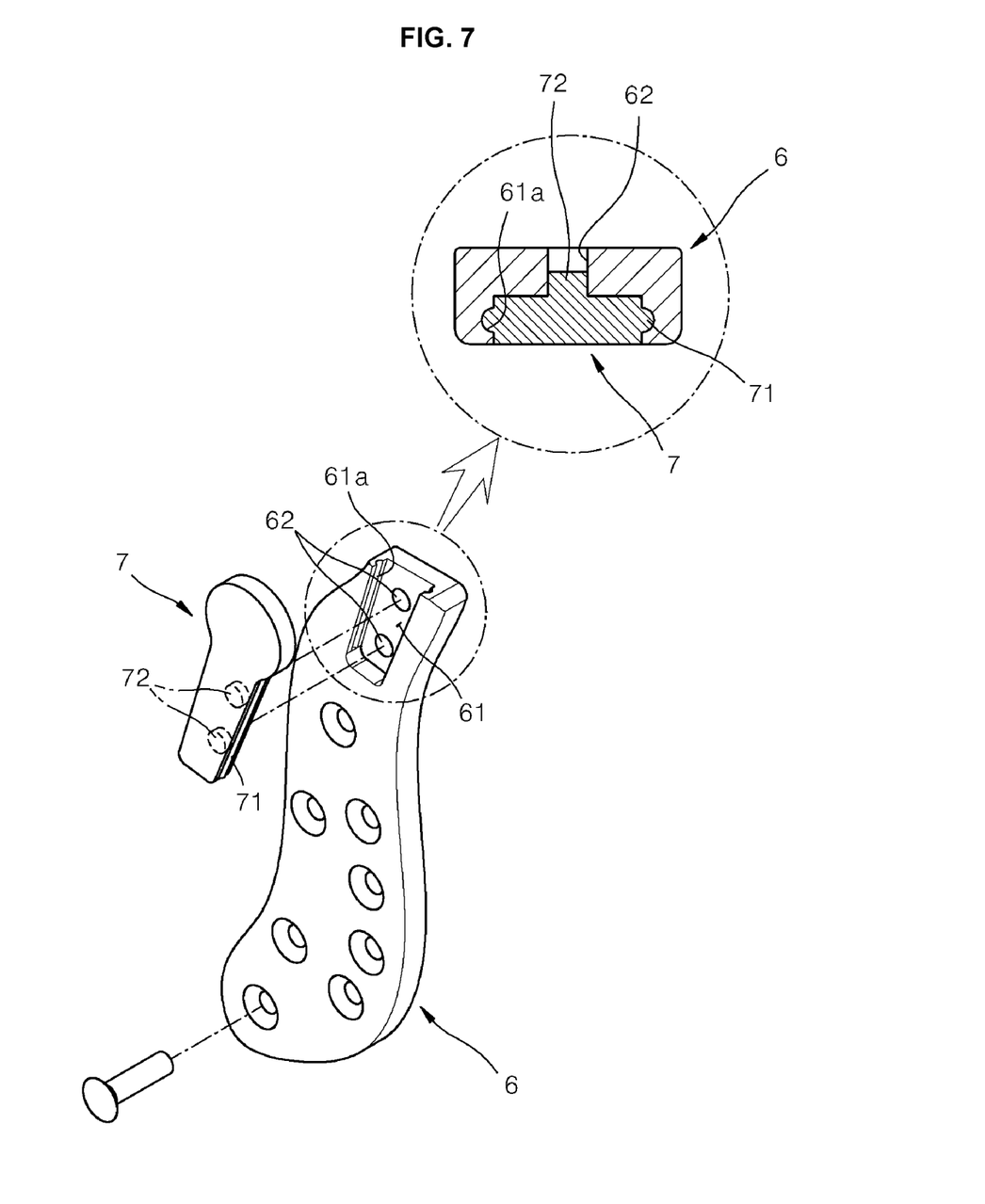
FIG. 7 is an exploded perspective view of a first plate and a main prothesis, according to another embodiment of the disclosure.

FIG. 7 is an exploded perspective view of a first plate 6 and a main prothesis 7, according to another embodiment of the disclosure.

The first plate 6 adopted in the present embodiment further includes a jamming groove portion 61*a* formed on a surface defining an insertion groove 61 of the first plate 6, and the main prothesis 7 further includes a jamming rib 71 inserted into and jammed in the jamming groove portion 61*a*, and thus a binding force between the first plate 6 and the main prothesis 7 may be further greatly secured without another fastening device.

Also, the present embodiment includes a self-combining device enabling the combining of the first plate 6 and the main prothesis 7 by using a structure thereof, without using a screw.

In other words, the self-combining device includes a combining boss 72 protruding at the main prothesis 7 in shape of a projection, and a forced fit groove 62 formed at the first plate 6.

The present embodiment having such a structure enables the combining of the main prothesis 7 and the first plate 6 by using the structures thereof without having to use a separate fastening device, such as a screw, thereby further improving simplification of the structure and convenience of a procedure.

The first plate 6 and the main prothesis 7 may be fixed by using the structures thereof as described above, but may also be further fixed by using a fixing unit, such as a separate screw.

Figure 8:
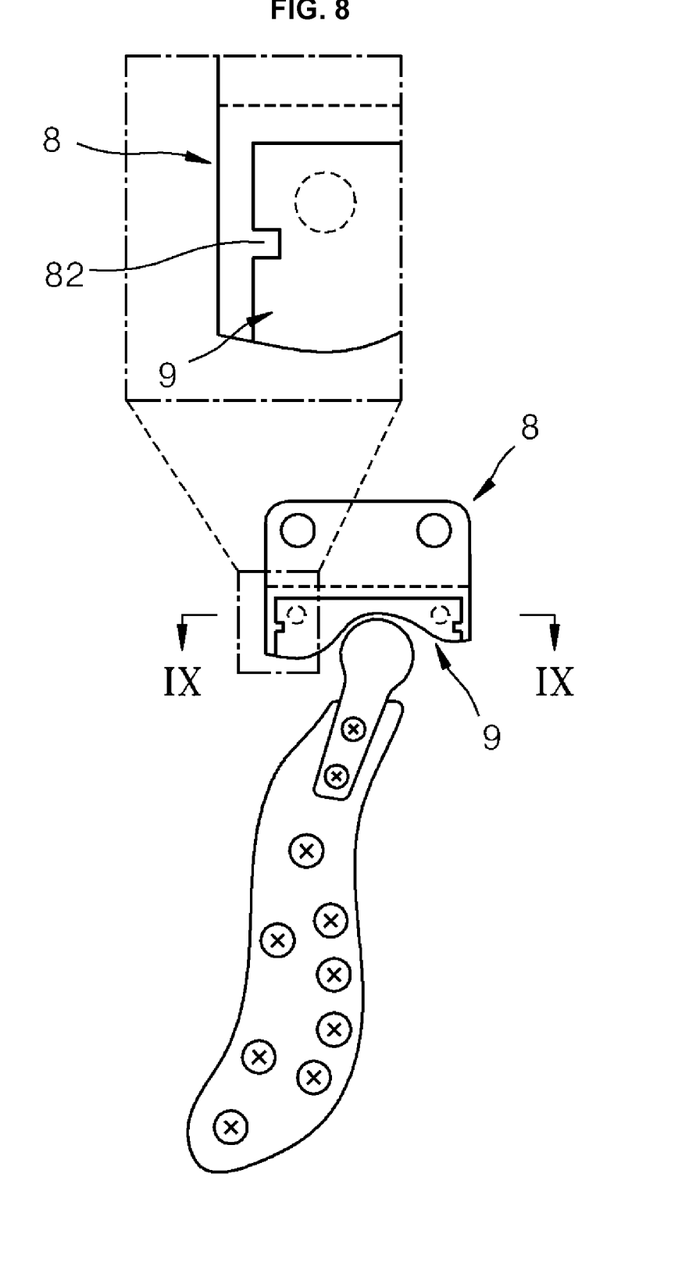
FIG. 8 is a partial cross-sectional side view of a second plate and a main prothesis, according to another embodiment of the disclosure.
Figure 9:
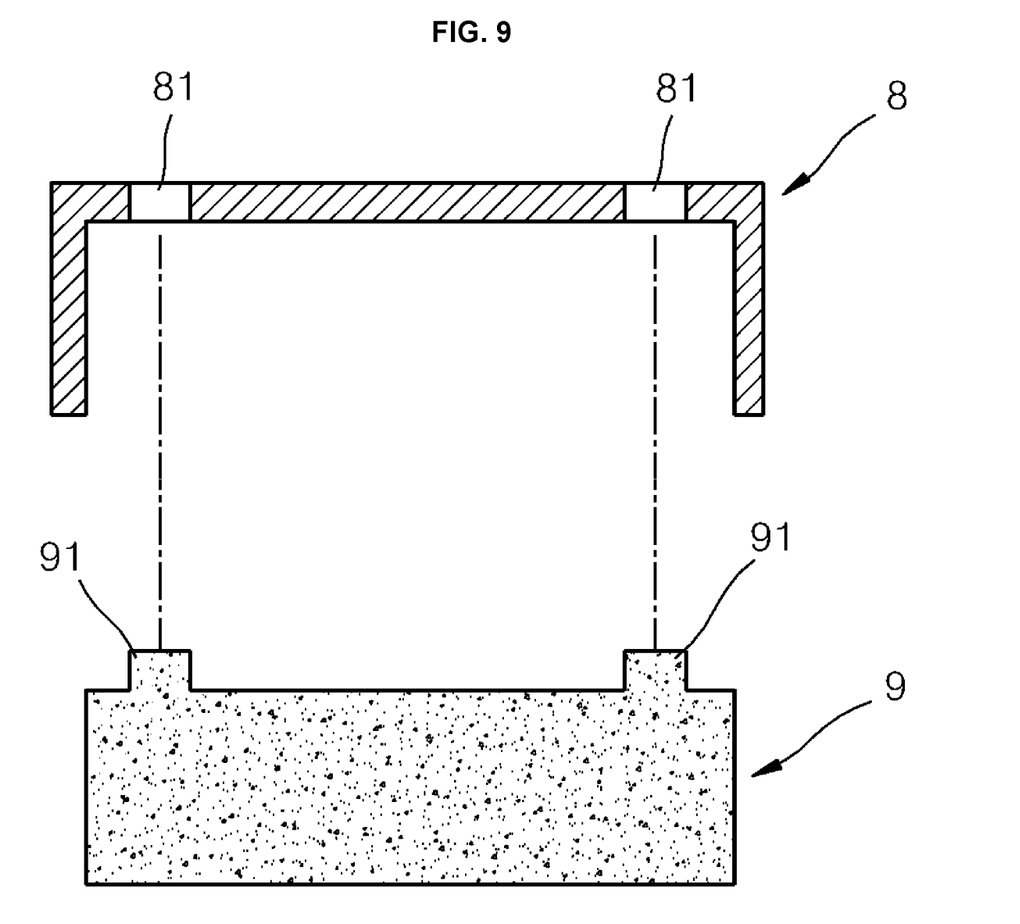
FIG. 9 is a cross-sectional view taken along a line IX-IX of FIG. 8.

FIG. 8 is a partial cross-sectional side view of a second plate 8 and the main prothesis 7, according to another embodiment of the disclosure, and FIG. 9 is a cross-sectional view taken along a line IX-IX of FIG. 8.

As shown in FIGS. 8 and 9, the present embodiment includes a sub-prothesis 9 detachably combined to the second plate 8. The sub-prothesis 9 is arranged such that a facing surface to the main prothesis 7 faces the main prothesis 7.

Also, the present embodiment includes a fitting groove 81 formed at the second plate 8 and a fitting protrusion 91 protruding at the sub-prothesis 9 such that the second plate 8 and the sub-prothesis 9 are smoothly combined with or separated from each other.

The present embodiment having such a structure is configured such that a part of a first plate, which is expected to be worn out by contacting the main prothesis 7, is smoothly replaced with the sub-prothesis 9, and thus only a part that is required to be replaced due to abrasion or damage is replaced, thereby improving convenience of a procedure and providing a high-quality medical service.

The second plate 8 includes a fixing protrusion 82 inserted into a detachment prevention groove provided at both sides of the sub-prothesis 9, such that a bonding force with the sub-prothesis 9 is greatly secured when the second plate 8 is combined to the sub-prothesis 9.

As such, like a fixing method between the first plate and the main prothesis 7, the second plate 8 and the sub-prothesis 9 may be fixed by using structures thereof, and may further be fixed by a fixing unit, such as a separate screw.

While various embodiments of the disclosure have been described above, the embodiments and the accompanying drawings are merely a part of the technical idea contained in the disclosure, and it would be obvious that modifications and specific embodiments easily inferred by one of ordinary skill in the art within the range of the technical idea included in the specification and drawings of the disclosure are all included in the scope of the disclosure.

What is claimed is:

1. A customized artificial temporomandibular joint unit comprising:
    a first plate configured to be provided along a lower line of a lower jawbone forming a temporomandibular joint and having an insertion groove that is outwardly open;
    a second plate configured to be provided at a temporal bone forming the temporomandibular joint together with the lower jawbone;
    a main prothesis detachably combined to the first plate without a separate fastening device by being forcibly fit into the insertion groove while approaching the first plate, and arranged in a customized manner at a facing surface location facing the second plate; and
    a sub-prothesis detachably combined to the second plate and having a facing surface to the main prothesis arranged to face the main prothesis, the sub-prothesis having a detachment prevention groove at both sides of the sub-prothesis,
    wherein the second plate includes a fixing protrusion inserted into the detachment prevention groove.

2. The customized artificial temporomandibular joint unit of claim 1, wherein the first plate comprises a jamming groove portion formed on a surface defining the insertion groove, and the main prothesis comprises a jamming rib inserted into the jamming groove portion.

3. The customized artificial temporomandibular joint unit of claim 1, wherein the main prothesis comprises:
    a combining portion forcibly fit into the insertion groove of the first plate; and
    a convex portion extending from the combining portion towards the second plate and having a surface facing the second plate convex in a ball shape,
    wherein the combining portion of the main prothesis has a tapered shape such that a width decreases towards the convex portion, and the insertion groove of the first plate has a shape corresponding to the combining portion.

4. The customized artificial temporomandibular joint unit of claim 1, further comprising:
    a fitting groove formed on the second plate; and
    a fitting protrusion protruding at the sub-prothesis to be detachably combined to the fitting groove.

* * * * *